United States Patent
Fear et al.

(10) Patent No.: US 7,454,242 B2
(45) Date of Patent: Nov. 18, 2008

(54) TISSUE SENSING ADAPTIVE RADAR IMAGING FOR BREAST TUMOR DETECTION

(76) Inventors: Elise Fear, c/o Suite 130, 3553 - 31 Street N.W., Calgary, Alberta (CA) T2L 2K7; Michal Okoniewski, c/o Suite 130, 3553 - 31 Street N.W., Calgary, Alberta (CA) T2L 2K7; Maria Stuchly, c/o Suite 130, 3553 - 31 Street N.W., Calgary, Alberta (CA) T2L 2K7

( * ) Notice: Subject to any disclaimer, the term of this patent is extended or adjusted under 35 U.S.C. 154(b) by 593 days.

(21) Appl. No.: 10/942,945

(22) Filed: Sep. 17, 2004

(65) Prior Publication Data
US 2005/0107693 A1    May 19, 2005

Related U.S. Application Data

(60) Provisional application No. 60/481,390, filed on Sep. 17, 2003.

(51) Int. Cl.
*A61B 5/05* (2006.01)
(52) U.S. Cl. .............. 600/430; 600/306; 600/407; 324/637; 324/638; 324/639; 324/642; 324/646; 343/700 R; 342/361; 607/101; 607/156
(58) Field of Classification Search ............ 600/430, 600/407, 437–461, 306; 324/639, 637, 638, 324/642, 646, 659; 343/700 R; 342/361; 607/101, 156
See application file for complete search history.

(56) References Cited

U.S. PATENT DOCUMENTS

| | | | | |
|---|---|---|---|---|
| 4,641,659 A | * | 2/1987 | Sepponen ............... | 600/430 |
| 4,805,627 A | * | 2/1989 | Klingenbeck et al. ....... | 600/425 |
| 5,481,196 A | * | 1/1996 | Nosov ................... | 324/637 |
| 5,662,110 A | * | 9/1997 | Carr ..................... | 600/430 |
| 5,704,355 A | | 1/1998 | Bridges ................. | 128/653.1 |
| 5,807,257 A | | 9/1998 | Bridges ................. | 600/430 |
| 5,829,437 A | | 11/1998 | Bridges ................. | 128/653.1 |
| 5,841,288 A | | 11/1998 | Meaney et al. ........... | 324/639 |
| 6,061,589 A | | 5/2000 | Bridges et al. .......... | 600/430 |
| 6,421,550 B1 | | 7/2002 | Bridges et al. .......... | 600/407 |
| 6,448,788 B1 | | 9/2002 | Meaney et al. ........... | 324/637 |

(Continued)

FOREIGN PATENT DOCUMENTS

WO    WO 02/25773 A1    3/2002

OTHER PUBLICATIONS

Meaney et. al., "A Clinical Prototype for Active Microwave Imaging of the Breast," IEEE Transactions on Microwave Theory and Techniques, vol. 48, No. 11, Nov. 2000.*

(Continued)

*Primary Examiner*—Brian L. Casler
*Assistant Examiner*—James R Talman
(74) *Attorney, Agent, or Firm*—Bennett Jones LLP

(57) ABSTRACT

A tissue-sensing adaptive radar method of detecting tumours in breast tissue uses microwave backscattering to detect tumours which have different electrical properties than healthy breast tissue. The method includes steps for reducing skin reflections and for constructing a three-dimensional image using synthetic focusing which shows the presence or absence of microwave reflecting tissues.

9 Claims, 5 Drawing Sheets

U.S. PATENT DOCUMENTS

| | | | |
|---|---|---|---|
| 2002/0067107 A1 | 6/2002 | Lewis | 310/334 |
| 2004/0077943 A1* | 4/2004 | Meaney et al. | 600/430 |
| 2004/0167399 A1* | 8/2004 | Li | 600/430 |

OTHER PUBLICATIONS

Fear et. al., "Microwave detection of breast tumors: comparison of skin subtraction algorithms," Proceedings of SPIE, vol. 4129, pp. 207-217, 2000.*

Meaney et al, "Microwave imaging for breast cancer detection: preliminary experience" publication, Proceedings of SPIE, vol. 3977, 2000, pp. 308-319.

Hagness, et al., "Two-Dimensional FDTD analysis of a pulsed micrwave confocal system for breast cancer detection: Fixed-focus and antenna-array sensors" publication IEEE Biomed. Eng. vol. 45, pp. 1470-1479, Dec. 1998.

Hagness, et al., "Three-Dimensional FDTD analysis of a pulsed microvave confocal system for breast cancer detection: Design of an antenna-array element", publication IEEE Trans. Antennas Propag., vol. 47, pp. 783-791, May 1999.

Li, et al., "A confocal microwave imaging algorithm for breast cancer detection", publication, IEEE Microwaves Wireless Comp. Lett., vol. 11, pp. 130-132, Mar. 2001.

Bond, et al., "Microwave imaging via space-time beamforming for early detection of breast cancer", publication, 2002 IEEE International Conference on Acoustics, Speech, and Signal Processing, vol. 3, 2002, pp. 2909-2912.

Ghodgaonkar, et al., "A Free-Space metnod of measurements of dielectric constants and loss tangents at microwave frequencies", publication, IEEE Trans. Instru. Meas. vol. 37, pp. 789-793, Jun. 1989.

Oimi, R., et al., "Non-destructive permittivity measurement of solid materials", publication, Meas. Sci. Tech., vol. 11, pp. 1623-1629, 2000.

Baker-Jarvis, J., et al. "Transmission-reflection and short-circuit line methods for measuring permittivity and permeability", publication, NIST Tech. Note 1355 (rev.), Dec. 1993.

Ulriksson, B., "Conversion of frequency-domain data to the time domain", publication, IEEE, vol. 74, pp. 74-77, Jan. 1986.

Frickey, D.A., "Using the inverse chirp-z transform for time-domain analysis of simulated radar signals," Publication, Proceedings of the 5th international conference on Signal Processing Applications and Technology, Dallas TX, Oct. 18-21, pp. 1366-1371, 1994.

Woody, C.D., "Characterization of an adaptive filter for the analysis of variable latency neuroelectric signals", publication, Medical Biological Eng. vol. 5, pp. 539-553, Feb. 1967.

Fear, E.C. "Microwave Imaging of the Breast", (invited), Article to appear in Technology in Cancer Research and Treatment, 2004.

Fear, E.C. et al., "A dielectric filled slotline bowtie antenna for breast cancer detection", article submitted Oct. 2004 to Electronics Letters.

Fear, E.C. et al., "Tissue sensing adaptive radar for breast cancer detection: a study of immersion liquids", article submitted 2004 to Electronics Letters.

Fear, et al., "Tissue sensing adaptive radar for breast tumor detection: investigation of issues for system implementation" article submitted to EMC 2005 Topical Meeting on Bi.

Fear, E.C. et al., "Comparison of immersion liquids for tissue sensing adaptive radar", Article Int. Sym. Antenna Technology, (2004) pp. 253-256.

Fear, E.C. et al., "Tissue sensing adaptive radar for breast cancer detection: investigations of reflections from the skin" Article 1EEE Antennas Symp. (2004).

Fear, E.C.et al. "Preliminary investigations of tissue sensing adaptive radar for breast tumor detetion", article 25th Annual Meeting of the IEEE, 2003, pp. 3787-3790.

Fear,E.C. et al., "A dielectric-filled ultrawideband antenna for breast cancer detection" article 1EEE Antennas Symp. 2003, pp. 218-221.

Fear, E.C.et al., "Experimental feasibility of breast tumor detection and localization," article 1EEE MTT-S Int'l symp. (2003) pp. 383-386.

Fear, E.C.et al., "Microwave system for breast tumor detection:experimental concept evaluation", 1EEE Antennas Symp. 2002, pp. 819-822.

Fear, E.C.et al., "Confocal microwave imaging for breast tumor detection:application to a hemispherical breast model", Article 1EEE MTT-S Symp. Digest, 2002 pp. 1759-1762.

Fear, E.C.et al., "Confocal microwave imaging for breast cancer detection: a study of resolution and detection ability", Article for 23rd Int'l Conference 1EEE Eng. (2001).

Fear, E.C.et al., "Confocal microwave imaging for breast tumor detection: comparison of immersion liquids", 1EEE Antennas Symp. Digest 2001, pp. 250-253.

Fear, et al. "FDTD Analysis of Planar and Cylindrical Antenna-Array Configurations for 3D Breast Tumour Localization using Confocal Microwave Imaging" IEEE Antennas Symp.2001.

Fear, E.C. et al., "Microwave detection of breast tumours: comparision of skin subtraction algorithms" Proceedings of SPIE, 2000, pp. 207-217.

Fear, E.C., et al., "A comparison of two system configurations for microwave detection of breast cancer", CD-ROM Proceedings Cong. (2000).

Fear, E.C., et al., "Microwave breast tumour detection: antenna design and charcterization" 1EEE Antennas Symp. (2000) 1076-1079.

Fear, E.C., et al., "Microwave breast cancer detection", Microwave Symp. Digest 2000, pp. 1037-1040.

Fear, E.C., et al., "Microwave for breast cancern detection?", 1EEEE Potentials (2003).

* cited by examiner

Antenna scan for skin outline.

Sample antenna locations for detection scan

TISSUE SENSING ADAPTIVE RADAR IMAGING FOR BREAST TUMOR DETECTION

CROSS REFERENCE TO RELATED APPLICATIONS

This application claims priority to U.S. Provisional Patent Application No. 60/481,390 filed on Sep. 17, 2003, the contents of which are incorporated herein by reference.

BACKGROUND OF INVENTION

The present invention relates to a method and apparatus for detection of tumors, and particularly tumors in human breast tissue.

The purpose of any imaging system for breast cancer detection is to assist in the diagnosis of early stage breast cancer. Currently, women are encouraged to participate in breast cancer screening programs utilizing mammography. Mammograms are x-rays images of a compressed breast, and are acknowledged to be the leading method of breast imaging currently available. While mammography is very sensitive to lesions in the breast, it has acknowledged limitations. For example, mammograms create images of the breast based on density differences and there may be only a slight difference in density between normal tissue and tumors. This is especially problematic for imaging women with dense breasts, which comprise a significant portion of the population. Another limitation is that a lesion may not be immediately diagnosed via a single mammogram. Further investigation of suspicious areas involves additional mammography, ultrasound and, in some cases, biopsy. Less than 10% of the suspicious areas investigated are diagnosed as cancer.

Every time a mammogram is taken, the patient incurs a small risk of having a breast tumor induced by the ionizing radiation properties of the X-rays used during the mammogram. Also, the process is sometimes imprecise and, as a result, not cost-efficient. Accordingly, the National Cancer Institute has not recommended mammograms for women under fifty years of age, who are not as likely to develop breast cancers as are older women. However, while only about twenty two percent of breast cancers occur in women under fifty, data suggest that breast cancer is more aggressive in pre-menopausal women.

Mammograms require interpretation by radiologists who can spot cancers between five and ten millimeters in diameter, and the prognosis is excellent in those cases. However, about ten to fifteen percent of tumors of this size and most tumors below this size are not detected. One study showed major clinical disagreements for about one-third of the same mammograms that were interpreted by a group of radiologists. Further, many women find that undergoing a mammogram is a decidedly painful experience.

These limitations have generated interest in alternative breast imaging methods. Many medical imaging technologies have been applied to this problem, including ultrasound and magnetic resonance ("MR") imaging. Ultrasound is often used to differentiate solid tumors from liquid cysts, but does not provide definitive information on whether a solid tumor is malignant or benign. MR imaging provides a map of the tissue distributions in the breast, and MR breast imaging usually involves injection of a contrast agent. The uptake and washout of the contrast agent in the vicinity of the suspicious lesion is monitored, however it may be difficult to provide a definitive diagnosis as malignancies generally do not have behavior that is consistently and distinctly different than benign lesions.

Therefore, there is a need in the art of medical imaging for a complementary breast imaging tool. Specifically, imaging tools that may be applied to women with suspicious mammograms to quickly and effectively indicate the presence or absence of a tumor would be of great value. The keys to a successful technology are the presence of a consistent contrast between normal breast tissues and malignant lesions, and a difference in the response of benign and malignant tissues. In other words, a physical basis for tumor detection must exist.

Microwave imaging for breast tumor detection is considered to be promising, as it is believed that there is a significant or detectable contrast in malignant, benign and normal tissues over a broad frequency range.

SUMMARY OF INVENTION

Several approaches to microwave breast imaging have been proposed, including tomography and radar-based methods. Tomography reconstructs a map of the electrical properties in the breast using measurements of energy transmitted through the breast. Radar-based approaches detect strongly scattering objects (tumors) using measurements of energy reflected from the breast. The present invention utilizes a radar-based approach.

Radar-based imaging methods may also be known as confocal microwave imaging (CMI). Reflections may be observed at a number of antennas located on the breast, and images may be created by summing the reflections or synthetically focusing these reflections. Synthetic focusing involves calculating the time-delay from each antenna to a focal point, and time-shifting and summing the recorded signals. If a tumor was located at the focal point, then reflections from the tumor add together, resulting in a large contribution to the image at that focal point location. With the focal point in normal tissues, reflections tend to add incoherently, resulting in a small contribution to the image. By scanning the focal point through the volume of interest and observing areas of strong reflection, tumor detection and localization is possible.

In one aspect, the invention may comprise a method of detecting the presence or absence of a tumor within a breast including skin and an interior volume, comprising the steps of:(a)illuminating the breast with microwaves from a plurality of locations and recording the reflections received at each location as a signal;(b)identifying a first skin reflection and a second skin reflection separated by a period of time and time-gating the signal by setting all data arriving before the first skin reflection and after the second skin reflection to zero;(c)creating a first estimate of reflections from the skin and subtracting said first skin reflections from each signal;(d) creating a second estimate of reflections from the skin for a single location from the signals received in at least two adjacent locations and subtracting the second skin reflections from each signal; and(e)constructing a three-dimensional image of the interior volume from the signals showing the presence or absence of microwave reflecting tissues.

BRIEF DESCRIPTION OF DRAWINGS

The invention will now be described by way of an exemplary embodiment with reference to the accompanying simplified, diagrammatic, not-to-scale drawings. In the drawings.

DETAILED DESCRIPTION

The present invention provides for a method and apparatus for tissue sensing adaptive radar imaging of breast tissue. When describing the present invention, all terms not defined herein have their common art-recognized meanings. As used herein, "microwave" means a comparatively short electromagnetic wave, especially one between about one millimeter and one meter in wavelength, and corresponding to a frequency range from 300 MHz to 300 GHz. The term "radar" refers to a method of detecting the presence and location of an object by detecting reflections of electromagnetic radiation from the object. Microwave imaging in medical situations is well described in a publication entitled "Medical Applications of Microwave Imaging", edited by L. E. Larsen and J. H. Jacobi, IEEE Press 1986, the contents of which are incorporated herein by reference. The term "tissue sensing" means a process of radar imaging which may distinguish between various tissues of the breast such as skin, glandular tissue, and tumors. The term "adaptive" means a process of radar imaging which incorporates signal manipulation steps to remove non-tumor reflective signals using localized or signal-specific information.

The system of the present invention may be described as a tissue-sensing adaptive radar system. The physical basis for breast tumor detection with microwave imaging is the contrast in dielectric properties of normal and malignant breast tissues. In general terms, the system includes a plurality of wideband antennas for illuminating the breast and collecting the reflections as well as a computer system for acquiring the data and synthesizing an image from the accumulated data. The system is able to isolate reflections coming from a specific location within a three-dimensional volume, which in the present instance, is defined by the volume of the breast. The following description is of a preferred embodiment of the invention, which is not intended to be limiting of the claimed invention.

Figure 1:
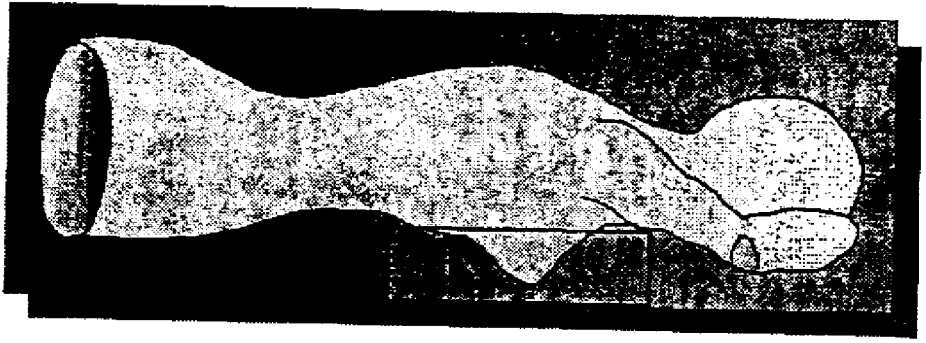
FIG. 1 is a schematic representation of a modified patient bed used in an imaging scan of the present invention.
Figure 1:
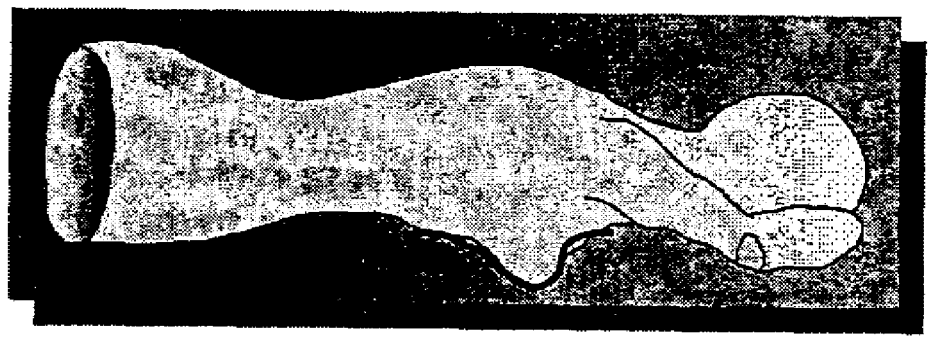

The preferred method of radar scanning in the present invention is referred to herein as "cylindrical" scanning. In a cylindrical scan, the patient lies face down on a modified patient bed which has a well for the breast to fall into. The well may include a gel or a liquid to better conform the breast to the surface of the well and the antennas. The antennas may be integrated into the surface of the well or may be moved around the well as shown in FIG. 1. In one embodiment, the antennas may be conformal antennas integrated by printing onto the surface of the well.

The antennas preferably comprise wideband antennas such as standard TEM horn antennas which are well known in the art. They may be adapted to effectively operate in a dielectric similar to either skin or fat tissue.

The present invention proceeds with data acquisition in two steps. First, an initial scan is performed to locate the breast in the imaging volume, and second, a tumor-sensing scan is performed to locate reflecting structures (such as a tumor) within the breast. The scans may be performed with a single antenna which is moved from location to location or a plurality of antennas in an array. It is not necessary that the initial scan be performed with microwaves as it is a boundary sensing step. It is possible to perform the initial scan with an alternative method such as using higher frequency signals which have shallower penetration or laser light.

Figure 2A:
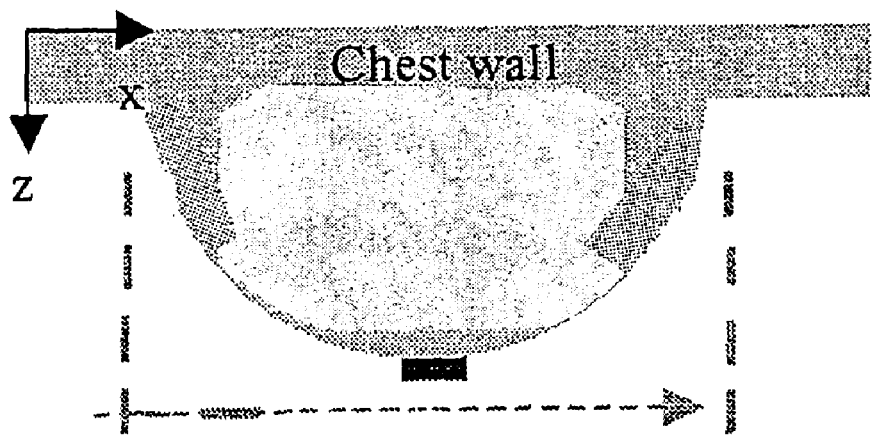
FIG. 2A is a schematic representation of the two-dimensional initial scan locations used to image or localize the skin.

The initial scan may be performed along one two-dimensional path or a set of two-dimensional paths as shown in FIG. 2A. The antenna may be moved (or multiple antennas provided) to a plurality of locations along the z direction, then a plurality of locations in the x direction, and finally a plurality of locations again in the z direction. With antennas integrated into the scanning bed, a subset of the antennas may be used for this scan.

Figure 2B:
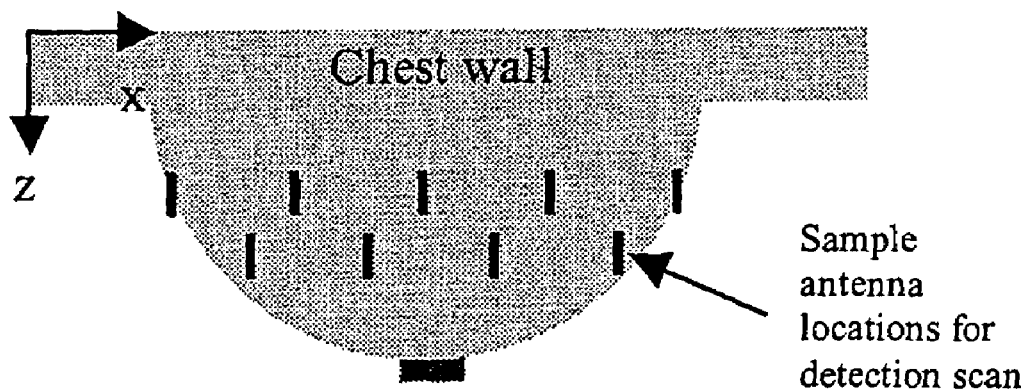
FIG. 2B is a schematic representation of the antenna locations used in a tumor detecting scan after the initial scan has taken place.

The tumor-sensing scan is preferably done to form a synthetic conical array. The antenna may be moved to a plurality of locations along a row (x-y plane), with multiple rows spanning from the nipple to the chest wall, as shown in FIG. 2B.

As most microwave measurement equipment is intended for use in the frequency domain, the measured data are in the frequency domain. In order to obtain reasonable resolution for the images and maintain compatibility with the image formation algorithms described herein, conversion to time domain signals is required. A weighting window is applied to the measured data to produce the desired time-domain pulse.

This pulse may be a differentiated Gaussian pulse with maximum frequency content near 5.24 GHz and full-width half-maximum (FWHM) bandwidth from 1.68 to 10 GHz. Any pulse with ultra-wideband frequency content in the range of 0.1 to 10 GHz may be suitable for use. The weighted signals are transformed to the time domain either with inverse Fourier transforms or, more preferably, inverse chirp-z transforms, both of which are well known in the art. The latter provide flexibility in selection of the time step and smaller time steps may assist in clutter reduction.

The recorded signals have early and late time content. The early time content is dominated by the incident pulse, reflections from the skin and residual antenna reverberations. The late time content contains tumor backscatter and backscatter due to clutter. The signal processing goals are to reduce the early-time content, which is of a much greater amplitude than the tumor response, and to selectively enhance the tumor response while suppressing the clutter to permit reliable detection of tumors in the reconstructed images. The images are reconstructed using the image formation steps described below.

Figure 3:
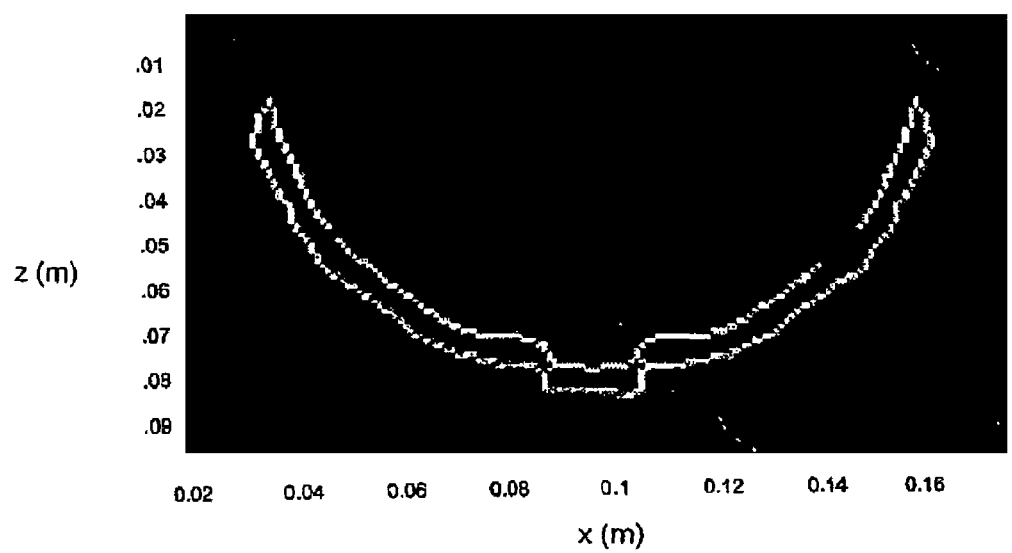
FIG. 3 is a representation of the image of skin resulting from a simulated two-dimensional skin sensing initial scan.
Figure 4A:
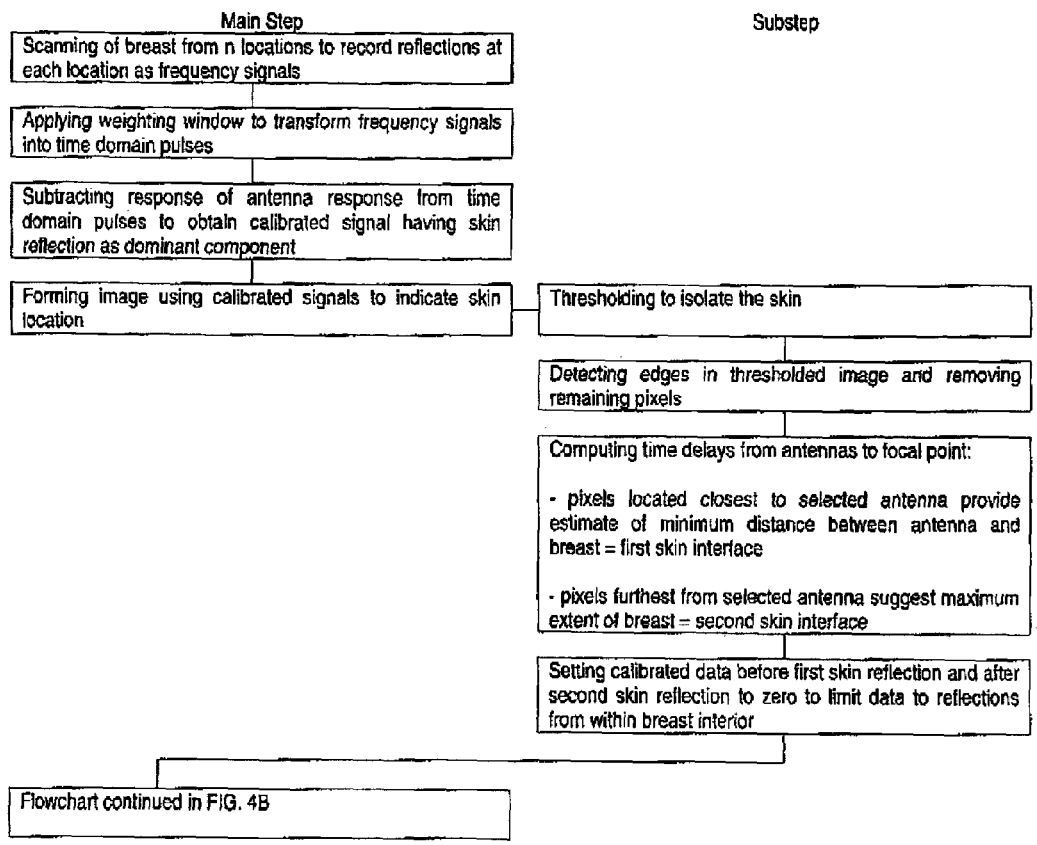
FIG. 4A is a flow diagram illustrating the sequence of data acquisition, initial processing, calibration, and skin-sensing steps.
Figure 4B:
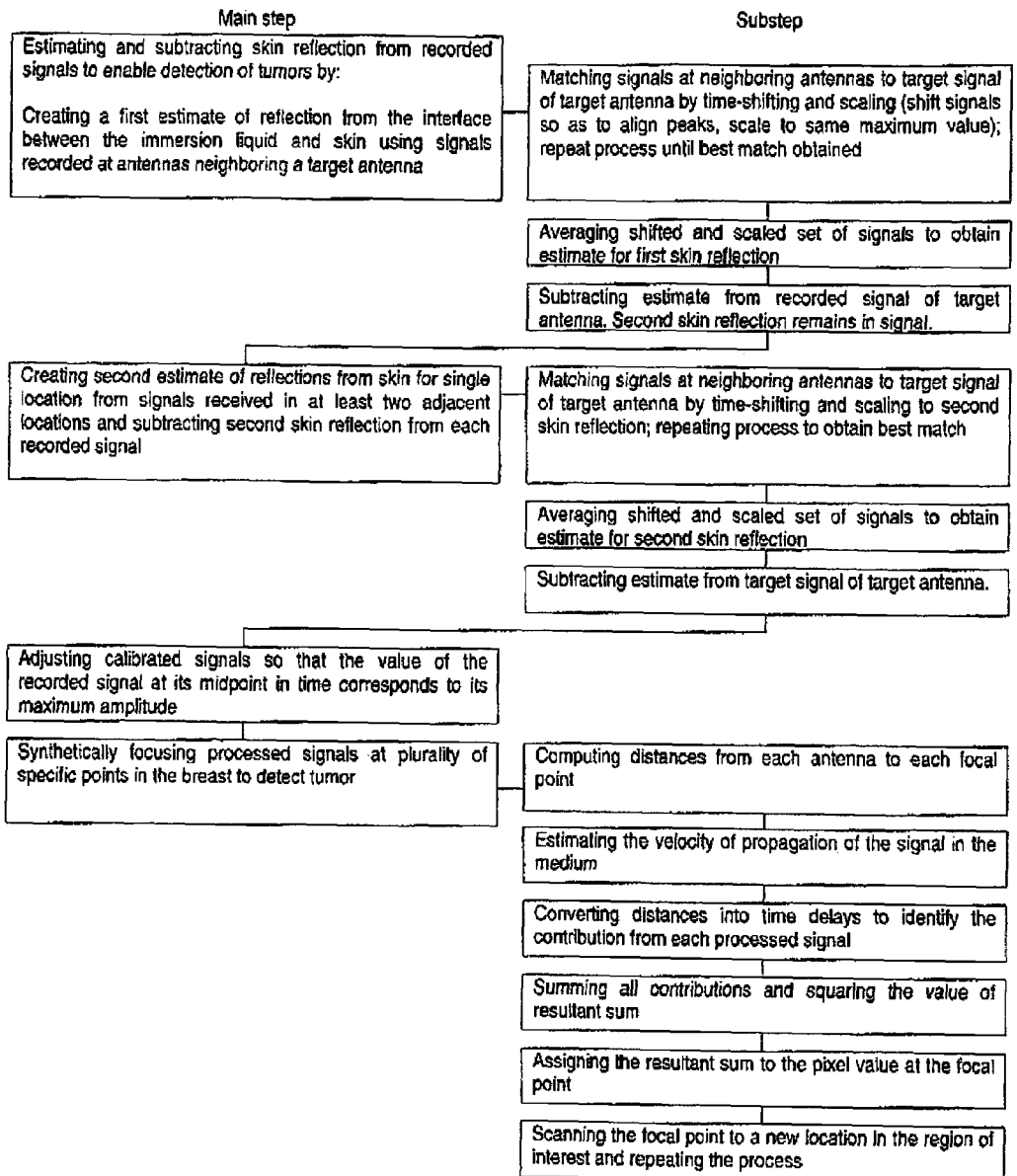
FIG. 4B is a flow diagram illustrating the sequence of first-skin-reflection reduction, second-skin-reflection reduction, and image-formation steps.

First, the signals are calibrated by removing the response of the antenna, which is done by subtracting the signal received at the antenna without any scattering object present. Next, an image is formed by synthetically scanning the focal point through the region inside the array. The resulting image indicates the location of the skin, and the imaging region for detection is defined using this information. The results of a simulated two-dimensional skin sensing scan is shown in FIG. 3. Thresholding or filtering of the image is used to identify the skin, edges are identified by the largest group of connected pixels and all other pixels are removed from the resulting image of the skin. The pixels located closest to and farthest away from each antenna are assumed to represent the first and second skin interfaces. The initial image of the skin formed from the initial skin-sensing scan is then used to determine an appropriate time-gate for the sensing scan data. In order to limit data to reflections from within the volume defined by the skin, the calibrated data arriving before the first skin reflection and after the second skin reflection are set to zero.

A two-step process may be used to reduce the reflection from the skin. These steps are applied to the signal recorded at each antenna or each location. The first step estimates the skin reflection using signals recorded at a number of antennas near the current antenna. The signal recorded at the current antenna is referred to as the target signal. The signals at neighboring antennas are matched to the target signal by time-shifting and scaling each signal in turn. This process is repeated several times in order to obtain the best match. The estimate of the target is obtained by taking the average of the shifted and scaled set of signals. A separate estimate is calculated for each antenna. The estimates are likely to be different, as each target signal requires different time-shifts and scaling. The estimate for each antenna is subtracted from the target signal. The resulting signal is likely to contain imperfectly cancelled reflections. This first step estimates the large reflection from the interface between the immersion liquid and the skin. A second reflection is generated from the interface between the skin and the interior of the breast. These reflections are likely similar at neighboring antennas, as the underlying tissues are expected to be somewhat similar.

The second step in the skin subtraction process provides an estimate of the reflections remaining in the signal after the first subtraction, which are related to local tissue variations. The estimate in this step is formed with the subtracted signals at the neighboring antennas. Again, the signals are scaled and time-shifted to match the target signal and the estimate is the average of the set of signals. This estimate is subtracted from the target signal. This two-step process may be referred to as "adaptive estimation" of the skin reflection.

The technique of adaptive estimation may also be used to estimate and subtract reflections from other strongly scattering objects, such as blood vessels and glandular tissue.

The calibrated signals, with greatly reduced skin and other non-tumor reflections, may then be adjusted such that the value of the signal at its midpoint in time corresponds to the maximum amplitude of the signal. For example, a differentiated Gaussian excitation signal has a zero-crossing at its centre point in time. The backscattered signal that would follow after a specific time delay corresponding to the round-trip distance between the antennas and the scattering object (tumor) would also have a zero-crossing at its centre point.

The processed signals are synthetically focused at a plurality of specific points in the breast. First, distances from each antenna to each focal point are computed and converted into time delays. Focusing includes a weighting based on relative distance between the focal point and antennas. In a preferred embodiment, path loss compensation is not required. The time delays are used to identify the contribution from each processed signal. All contributions are summed and the squared value of this sum is assigned to the pixel value at the focal point. An estimate of the velocity of propagation of the signal in the medium is used. The focal point is scanned to a new location in the region of interest, and this process is repeated. The focal point coordinates are defined with respect to the defined volume within the skin. Focusing may include a weighting based on relative distance between the focal point and antennas. This gives greater emphasis to data recorded at antennas located near the focal point. It may also be preferable to filter the image to emphasize pixels nearer the center of the scanned volume.

In one embodiment, the microwave imaging of the present invention may be combined with other imaging methods such as magnetic resonance (MR) techniques. MR images provide excellent definition of various tissue types, and blood vessels larger than about 1 mm may be imaged with time-of-flight angiography, as is well known in the art. The comparison or co-registration of MR and microwave images provides complementary information for image interpretation. For example, clutter in a microwave radar image may be identified as arising from tissue structures in the breast, or a lesion that enhances in a MR scan may be shown to be a strongly scattering object in a microwave image.

As will be apparent to those skilled in the art, various modifications, adaptations and variations of the foregoing specific disclosure can be made without departing from the scope of the invention claimed herein. The various features and elements of the described invention may be combined in a manner different from the combinations described or claimed herein, without departing from the scope of the invention.

The following references are incorporated herein as if reproduced in their entirety.

REFRENCES

[1] P. M. Meaney, K. D. Paulsen and M. W. Fanning, "Microwave imaging for breast cancer detection: preliminary experience," *Proceedings of SPIE*, vol. 3977, 2000, pp. 308-319.

[2] S. C. Hagness, A. Taflove, and J. E. Bridges, "Two dimensional FDTD analysis of a pulsed microwave confical system for breast cancer detection: Fixed-focus and antenna-array sensors," *IEEE Trans. Biomed. Eng.*, vol. 45, pp. 1470-1479, December 1998.

[3] S. C. Hagness, A. Taflove, and J. E. Bridges, "Three-dimensional FDTD analysis of a pulsed microwave confocal system for breast cancer detection: Design of an antenna-array element," *IEEE Trans. Antennas Propag.*, vol. 47, pp. 783-791, May 1999.

[4] E. C. Fear, X. Li, S. C. Hagness and M. A. Stuchly, "Confocal microwave imaging for breast tumour detection: localization of tumours in three dimensions," *IEEE Trans. Biomed. Eng.*, vol. 49, pp. 812-822, August 2002.

[5] X. Li and S. C. Hagness, "A confocal microwave imaging algorithm for breast cancer detection," *IEEE Microwave Wireless Comp. Lett.*, vol. 11, pp. 130-132, March 2001.

[6] E. C. Fear, J. Sill and M. A. Stuchly, "Experimental feasibility study of confocal microwave imaging", *IEEE Trans. Microw. Theory Tech.*, accepted, September 2002.

[7] E. J. Bond, E. J. Bond, X. Li. S. C. Hagness, and B. D. Van Veen, "Microwave imaging via space-time beamforming for early detection of breast cancer", 2002 *IEEE International Conference on Acoustics, Speech, and Signal Processing*, vol. 3, 2002, pp. 2909-2912.

[8] D. K. Ghodgaonkar, V. V. Varadan, and V. K. Varadan, "A free-space method of measurements of dielectric constants and loss tangents at microwave freqencies", *IEEE Trans. Instru. Meas.*, vol. 37, pp. 789-793, June 1989.

[9] R. Olmi, M. Bini, A. Ignesti and C. Riminesi, "Non-destructive permittivity measurement of solid materials", *Meas. Sci. Technol.*, vol. 11, pp. 1623-1629, 2000.

[10] J. Baker-Jarvis, M. D. Janezic, J. H. Grosvenor Jr., R. G. Geyer, "Transmission-reflection and short-circuit line methods for measuring permittivity and permeability", *NIST Technical Note* 1355 (revised), December 1993.

[11] B. Ulriksson, "Conversion of frequency-domain data to the time domain," *Proc. IEEE*, vol. 74, pp. 74-77, January 1986

[12] D. A. Frickey, "Using the inverse chirp-z transform for time-domain analysis of simulated radar signals," *Proceedings of the 5th International Conference on Signal Processing Applications and Technology*, Dallas, Tex., USA, October 18-21, pp.1366-1371, 1994.

[13] A. Taflove and S. C. Hagness, *Computational Electrodynamics: The Finite-Difference Time-Domain Method*, 2nd ed., Artech House: Boston, 2000.

[14] C. D. Woody, "Characterisation of an adaptive filter for the analysis of variable latency neuroelectric signals", *Medical Biological Eng.*, vol. 5, pp. 539-553, February 1967.

The invention claimed is:

1. A method of detecting the presence or absence of a tumour within a breast comprising skin and an interior volume, comprising the steps of:
   (a) illuminating the breast with microwaves from a plurality of locations and recording the reflections received at each location as a signal;
   (b) identifying a first skin reflection and a second skin reflection separated by a period of time and time-gating the signal by setting all data arriving before the first skin reflection and after the second skin reflection to zero;
   (c) creating a first estimate of reflections from the skin and subtracting said first skin reflections from each signal;
   (d) creating a second estimate of reflections from the skin for a single location from the signals received in at least two adjacent locations and subtracting the second skin reflections from each signal;
   (e) constructing a three-dimensional image of the interior volume from the signals showing the presence or absence of microwave reflecting tissues.

2. The method of claim 1 further comprising the step of adaptively estimating reflections from strongly reflecting non-tumour tissue within the interior volume and subtracting such reflections from the signals.

3. The method of claim 1 wherein the image construction step comprises focusing based on relative distance between the focal point and the antenna.

4. The method of claim 3 wherein the image reconstruction step is free of a path loss compensation step.

5. The method of claim 3 wherein the resulting image is filtered to emphasize locations closer to the centre of the breast, away from the antenna.

6. The method of claim 1 further comprising the step of co-registering a magnetic resonance image of the same breast and comparing features between the microwave radar image and the magnetic resonance image.

7. The method of claim 1 further comprising the steps of creating a first estimate of reflections from a non-tumour reflecting structure within the interior volume and subtracting said non-tumour reflections from each signal; and creating a second estimate of reflections from the non-tumour reflecting structure for a single location from the signals received in at least two adjacent locations and subtracting the second estimate from each signal.

8. The method of claim 1 wherein a person whose breast is being scanned lies face down while being scanned.

9. A method of detecting the presence or absence of a tumour within a breast comprising skin and an interior volume, comprising the steps of:
   (a) illuminating the breast with microwaves from a plurality of locations and recording the reflections received at each location as a signal;
   (b) identifying a first skin reflection and a second skin reflection separated by a period of time and time-gating the signal by setting all data arriving before the first skin reflection and after the second skin reflection to zero;
   (c) creating a first estimate of reflections from the skin and subtracting said first skin reflections from each signal;
   (d) adaptively estimating reflections from strongly reflecting non-tumour tissue within the interior volume and subtracting such reflections from the signals by
      (i) creating a second estimate of reflections from the skin for a single location from the signals received in at least two adjacent locations and
      (ii) subtracting the second skin reflections from each signal;
   (e) constructing a three-dimensional image of the interior volume from the signals showing the presence or absence of microwave reflecting tissues.

* * * * *